United States Patent
Niazi

(10) Patent No.: US 9,284,346 B2
(45) Date of Patent: Mar. 15, 2016

(54) PREPARATIVE CHROMATOGRAPHY COLUMN AND METHODS

(75) Inventor: Sarfaraz K. Niazi, Deerfield, IL (US)

(73) Assignee: Therapeutic Proteins International, LLC, Chicago, IL (US)

(*) Notice: Subject to any disclaimer, the term of this patent is extended or adjusted under 35 U.S.C. 154(b) by 611 days.

(21) Appl. No.: 13/246,830

(22) Filed: Sep. 27, 2011

(65) Prior Publication Data

US 2012/0018380 A1     Jan. 26, 2012

(51) Int. Cl.
| | |
|---|---|
| C07K 1/14 | (2006.01) |
| B01J 20/28 | (2006.01) |
| C07K 1/16 | (2006.01) |
| C07K 1/18 | (2006.01) |
| C07K 1/20 | (2006.01) |
| C07K 1/22 | (2006.01) |
| B01D 15/22 | (2006.01) |

(52) U.S. Cl.
CPC ............... *C07K 1/14* (2013.01); *B01J 20/2805* (2013.01); *C07K 1/165* (2013.01); *C07K 1/18* (2013.01); *C07K 1/20* (2013.01); *C07K 1/22* (2013.01); *B01D 15/22* (2013.01)

(58) Field of Classification Search
CPC ....... B01J 20/2805; C07K 1/14; C07K 1/165; C07K 1/18; C07K 1/20; C07K 1/22; B01D 15/22
USPC ........................................ 210/635, 656, 198.2
See application file for complete search history.

(56) References Cited

U.S. PATENT DOCUMENTS

| | | | | |
|---|---|---|---|---|
| 2,087,157 | A * | 7/1937 | Lind | 141/2 |
| 2,456,524 | A * | 12/1948 | Meincke, Jr. | 210/257.2 |
| 4,169,048 | A * | 9/1979 | Albers, Sr. | 210/603 |
| 4,550,594 | A * | 11/1985 | Engstrom | 73/61.53 |
| 4,668,379 | A * | 5/1987 | Rosensweig et al. | 208/157 |
| 5,167,809 | A * | 12/1992 | Mann et al. | 210/198.2 |
| 5,368,753 | A * | 11/1994 | Gardenier, Jr. | 210/800 |
| 5,423,982 | A * | 6/1995 | Jungbauer et al. | 210/198.2 |
| 5,547,586 | A * | 8/1996 | Halperin et al. | 210/686 |
| 5,618,105 | A * | 4/1997 | Baker | 366/130 |
| 5,993,656 | A * | 11/1999 | Cordani | 210/282 |
| 6,043,067 | A * | 3/2000 | Lihme et al. | 435/174 |
| 6,214,221 | B1* | 4/2001 | Koft | |
| 6,383,380 | B1* | 5/2002 | Kopf | 210/198.2 |
| 6,797,174 | B2* | 9/2004 | Neuroth et al. | 210/656 |
| 7,682,505 | B2* | 3/2010 | Vidalinc | 210/198.2 |
| 2002/0094568 | A1* | 7/2002 | Hei | 435/308.1 |
| 2004/0129641 | A1* | 7/2004 | Paananen et al. | 210/656 |
| 2005/0054839 | A1 | 3/2005 | Purdum | |
| 2005/0236312 | A1* | 10/2005 | Gebauer | 210/198.2 |
| 2006/0176767 | A1* | 8/2006 | Hlavinka et al. | 366/197 |

(Continued)

FOREIGN PATENT DOCUMENTS

EP       1808700 A2      7/2007
WO    2011/076386 A1    6/2011

OTHER PUBLICATIONS

International Search Report and Written Opinion dated Dec. 17, 2012, for International Application No. PCT/US12/57188.

*Primary Examiner* — Ernest G Therkorn
(74) *Attorney, Agent, or Firm* — Therapeutic Proteins International, LLC; Sarfaraz K. Niazi; Cheryl Liljestrand

(57) ABSTRACT

A chromatography column that captures components in a process liquid in a free flow state and allows elution in steps is described.

4 Claims, 4 Drawing Sheets

(56) References Cited

U.S. PATENT DOCUMENTS

| | | |
|---|---|---|
| 2007/0219524 A1* | 9/2007 | Burnouf et al. ............... 604/408 |
| 2007/0221557 A1* | 9/2007 | Barber et al. ............... 210/198.2 |
| 2007/0295667 A1* | 12/2007 | Ruprecht ..................... 210/693 |
| 2008/0118967 A1* | 5/2008 | Korpela et al. ............... 435/174 |
| 2008/0314832 A1* | 12/2008 | Umezawa et al. ............ 210/635 |
| 2011/0198286 A1* | 8/2011 | Niazi ............................. 210/638 |
| 2012/0016113 A1* | 1/2012 | Niazi ............................. 530/417 |

\* cited by examiner

PREPARATIVE CHROMATOGRAPHY COLUMN AND METHODS

FIELD OF THE INVENTION

The present invention relates to preparative chromatography columns and method of their use.

BACKGROUND OF THE INVENTION

Chromatography columns are used in industrial process to purify process liquids and separate the components of interest from process liquids. Prior art chromatography columns comprise a column generally in the form of hollow cylinder, which is packed with a chromatography media and the process liquid passed through the media to cause the binding of the components of the process liquid to the chromatography media. Once the components of the process liquid are loaded onto column, the chromatography media are eluted with solutions of various pH and electrolyte concentrations to obtain a purified form of the components. These processes are tedious, slow, and expensive and cause breakdown of the components during the process of purification.

There is an unmet need to create a chromatography column that will reduce the process time substantially, requires smaller capital investment and offers a sustainable cost of production advantage over a long time.

The present invention offers a column and a method of its use wherein the components are bound to the chromatographic media in a free flow form instead of in a packed column; once bound, the liquid is removed and the bound components eluted in steps to obtain a pure form. Alternately, once the components have become bound, the chromatographic media can be transferred to a traditional column for further purification.

SUMMARY OF THE INVENTION

According to the present invention, several problems associated with the use of traditional chromatography columns have been resolved, the cost of manufacturing components from a process liquid reduced and the need for expensive equipment obviated.

The basic principle of chromatography involves a binding or association between a component and the media; these interactions can be ionic, polar, hydrophobic, specific molecular or physical capture. Once a chromatography media has been saturated with the components, it is eluted using buffers of different pH or electrolyte level to break the binding and the eluent collected containing a higher concentration of the components. In many instances, gradient elution is performed where the characteristic of the buffer changes continuously causing a gradual breakdown of the binding of components and thus causing a separation of the components form impurities.

The gradient elution is a form of step elution where the steps are extremely small but it is also a continuous process that does refine the separation profile yet the step elution can be equally effective and all instances much faster than the gradient elution. The free flow binding of the components to chromatographic media as described in the present invention works best with a step elution process. At each step, the chromatography media is allow to come to a complete equilibration with the buffer added and then the entire content of the buffer is removed and replaced with another buffer with different properties. The method can be modified to use as a gradient system but that causes continuous dilution of the components eluted and reduces the purification profile.

BRIEF DESCRIPTION OF THE FIGS.

DETAILED DESCRIPTION OF THE INVENTION

Historically the columns used in preparative chromatography are vertical cylindrical tubes packed with chromatography media intended to bind the target molecules and then elute them slowly with a buffer and collecting various fractions of the eluent. The fractions containing the target molecule in its purest form are then pooled to obtain a desired degree of purification.

The methods of preparative chromatography are borrowed from the methods of chromatography used for analytical separation of components such as the use of high pressure to improve the separation efficiency. In preparative chromatography, it is the completeness of binding and the ability to elute is more important. There are many complexities in operating these columns one being a long time needed to load the column with a process liquid containing a target molecule such as a protein. Surprisingly, the fact that the target molecule will bind with the chromatography media in any environment suitable for such binding and it is not necessary to force a process liquid through a column to achieve the binding has been ignored in every current design of columns used in preparative chromatography. The present invention obviates the need for long loading times and additionally introduces methods that allow step elution to purify the target molecules without the need for typical rigid columns and their associated hardware including pumps, pipes, controllers etc.

Figure 1:
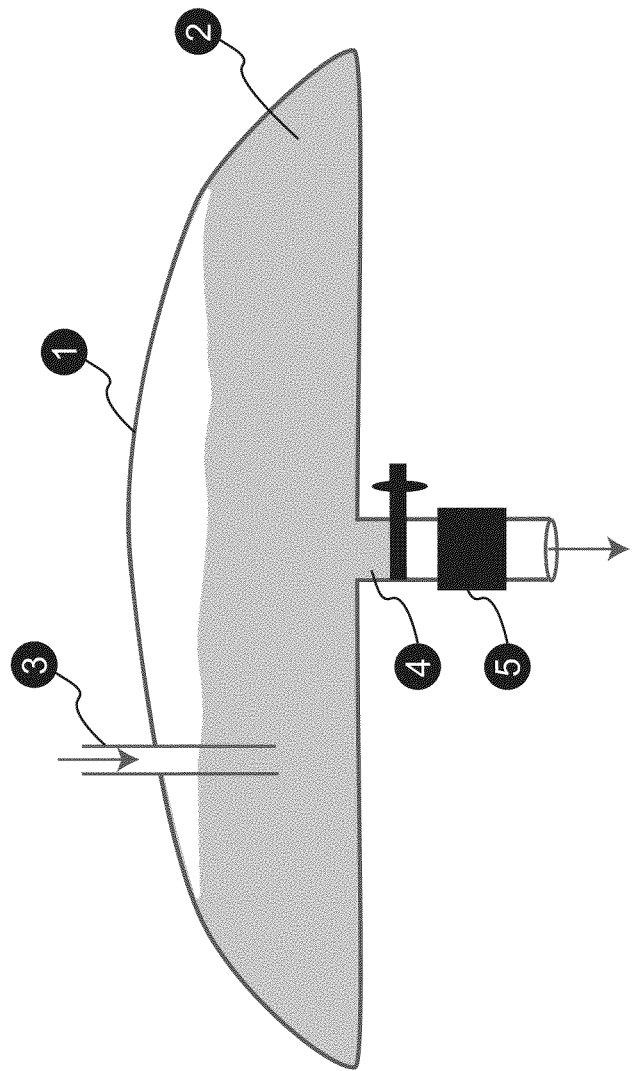
FIG. 1 shows a cross-sectional view of a first embodiment of a chromatography column in accordance with the present invention.

A first preferred embodiment of the invention is shown in FIG. 1 where a flexible container 1 containing chromatography media 2, a process liquid inlet 3, a process liquid outlet 4, a filter 5 to retain the chromatography media. The invention is operated by adding a process liquid through inlet 3 and the housing 2 allowed to stand for sufficient time to allow complete binding of the components in process liquid with the chromatography media. Not shown in the figure are optional means of agitating the liquid in the housing to reduce the binding time. These can involve shaking, vibrating or rocking the bag as shown, or stirring the liquid inside using a magnetic stirrer or an impeller. While these additional means will improve the rate of binding, these are not necessary; over time, the chromatography media and the components will bind if the conditions of binding are optimum.

Figure 2:
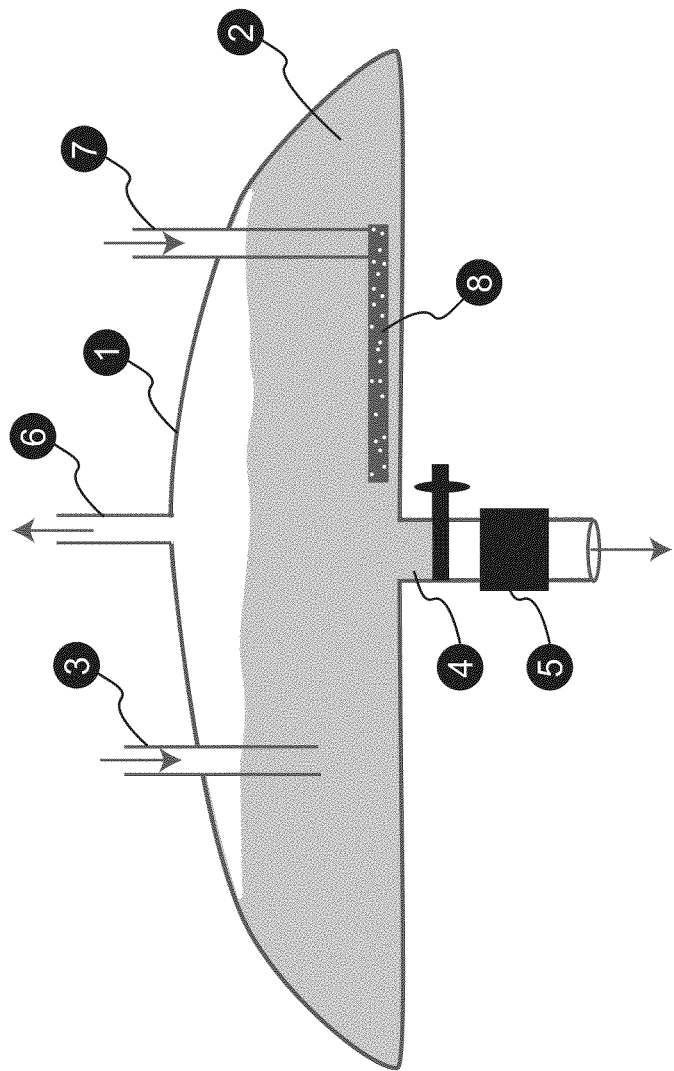
FIG. 2 shows a cross-sectional view of a second embodiment of a chromatography column in accordance with the present invention.

A second preferred embodiment of the invention is shown in FIG. 2 where an additional feature comprising a sparging rod 8 connected to a source of air 7 to pass a gas inside the housing to stir the liquid. This feature enhances the mixing and binding of chromatography media and the components; also included is an exhaust 6 to remove the gas used for sparging.

Figure 3:
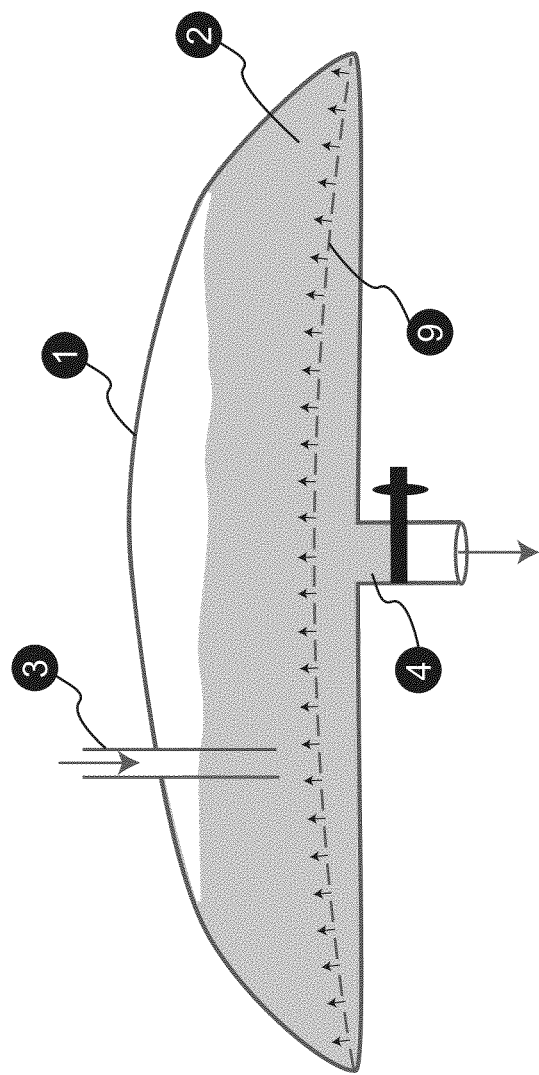
FIG. 3 shows a cross-sectional view of a third embodiment of a chromatography column in accordance with the present invention.

A third preferred embodiment is shown in FIG. 3 where an additional feature wherein a perforated septum 9 is installed in the housing and the filter 5 removed; the pore size of the septum is smaller than the size of chromatography media and thus acts as a filter; with its large surface area, it enhance the passage of liquid through the outlet 4. It is also possible to combine the features of FIGS. 2 and 3 to achieve a system wherein gas from sparger agitates the liquid while a perforated septum acts as a filter.

Figure 4:
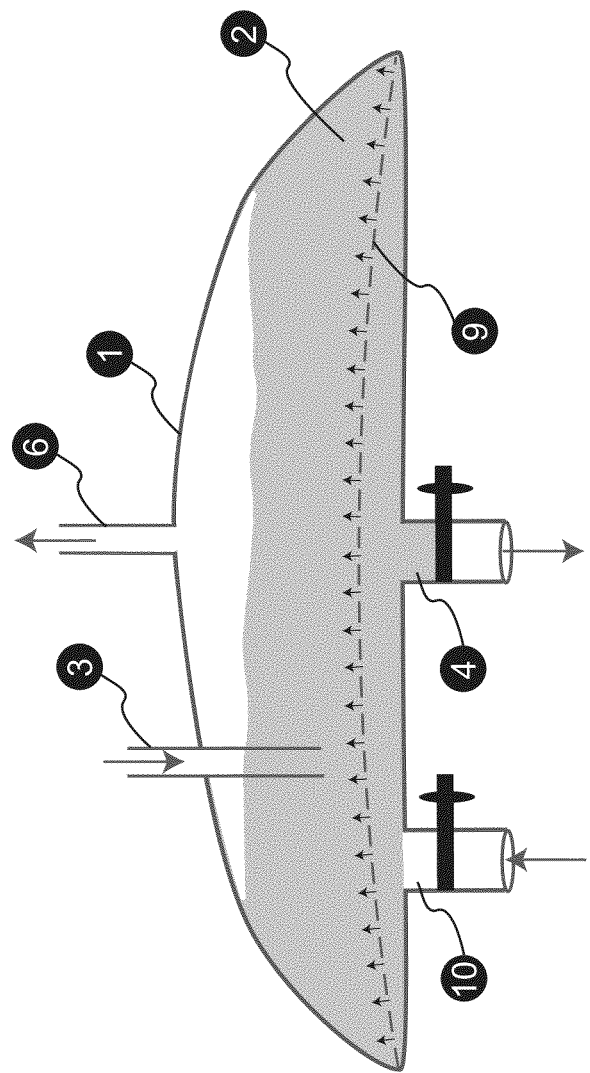
FIG. 4 shows a cross-sectional view of a fourth embodiment of a chromatography column in accordance with the present invention.

A fourth preferred embodiment is shown in FIG. 4 shows a further extension of the embodiment presented in FIG. 3; here an additional feature of gas inlet at the bottom of the housing is introduced; the gas entering the lower chamber below the septum then acts as a pressure chamber, forcing air out of the pores of the septum producing agitation of liquid.

Whereas the preferred embodiments described in FIGS. 1-4 depict a flexible bag alone, it is implied that if a method of enhanced mixing is used then additional features like placing the bags on a shaker or rocking them or using an ultrasonic energy will be used. The housing structure described in FIGS. 1-4 can also take form of a hard-walled system, metallic or non-metallic and of any possible shape as the efficiency of the column is not dependent on the shape of the vessel. The only requirement of the invention is that there be enough room in the housing to allow a free flow mixing of the chromatographic media with the process liquid and sufficient time allowed to equilibrate. The same holds true for the process time at all steps of step elution.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A disposable preparative chromatography column for effecting separation of components of a process liquid comprising:
   a. a flexible disposable bag with an inner volume;
   b. a septum disposed within the flexible disposable bag to separate the flexible disposable bag into a flexible upper chamber and a flexible lower chamber, the septum including a porous surface that allows passage of liquid but not chromatography media from the upper chamber to the lower chamber;
   c. a chromatography media disposed in the upper chamber;
   d. at least one inlet to introduce liquid into the flexible upper chamber of the bag containing the chromatography media;
   e. at least one outlet to remove the liquid from the flexible lower chamber of the bag after passage through the septum; and
   f. at least one mixing mechanism to mix the contents of the bag.

2. The disposable preparative chromatography column of claim 1, wherein the flexible disposable bag includes an upper sheet and a lower sheet that form the inner volume, and wherein the septum is attached to at least the lower sheet.

3. The disposable preparative chromatography column of claim 2, wherein a cross-sectional length of the septum is longer than a cross-sectional length of the lower sheet.

4. The disposable preparative chromatography column of claim 1, which includes a gas inlet configured to inject air into the lower chamber.

* * * * *